United States Patent
Suzukamo et al.

(10) Patent No.: US 10,045,957 B2
(45) Date of Patent: Aug. 14, 2018

(54) GIP ELEVATION INHIBITOR

(75) Inventors: Chika Suzukamo, Utsunomiya (JP); Koji Onizawa, Mooka (JP); Noriko Osaki, Utsunomiya (JP)

(73) Assignee: KAO CORPORATION, Tokyo (JP)

(*) Notice: Subject to any disclaimer, the term of this patent is extended or adjusted under 35 U.S.C. 154(b) by 96 days.

(21) Appl. No.: 14/343,640

(22) PCT Filed: Sep. 14, 2012

(86) PCT No.: PCT/JP2012/073644
§ 371 (c)(1),
(2), (4) Date: Mar. 7, 2014

(87) PCT Pub. No.: WO2013/039210
PCT Pub. Date: Mar. 21, 2013

(65) Prior Publication Data
US 2014/0221483 A1    Aug. 7, 2014

(30) Foreign Application Priority Data
Sep. 15, 2011 (JP) .................. 2011-201406

(51) Int. Cl.
*A61K 31/232*    (2006.01)
*A23L 33/10*    (2016.01)

(52) U.S. Cl.
CPC ............ *A61K 31/232* (2013.01); *A23L 33/10* (2016.08)

(58) Field of Classification Search
None
See application file for complete search history.

(56) References Cited

U.S. PATENT DOCUMENTS

| | | | |
|---|---|---|---|
| 2002/0009481 A1 | 1/2002 | Nadachi et al. | |
| 2003/0157107 A1 | 8/2003 | Miyawaki et al. | |
| 2005/0002988 A1 | 1/2005 | Mizumoto et al. | |
| 2008/0064750 A1 | 3/2008 | Masui et al. | |
| 2009/0143277 A1 | 6/2009 | Mizumoto et al. | |
| 2009/0192223 A1 | 7/2009 | Takeno et al. | |

FOREIGN PATENT DOCUMENTS

| | | |
|---|---|---|
| CN | 1946301 A | 4/2007 |
| CN | 101426491 A | 5/2009 |
| JP | 10-231495 A | 9/1998 |
| JP | 3545760 B2 | 4/2004 |
| JP | 2005-336471 A | 12/2005 |
| JP | 2006-342084 A | 12/2006 |
| JP | 2007-262014 A | 10/2007 |
| JP | 2007-290989 A | 11/2007 |
| JP | 2010-180203 A | 8/2010 |
| WO | WO 01/87341 A1 | 11/2001 |
| WO | WO 2008/054192 A1 | 5/2008 |

OTHER PUBLICATIONS

Naitoh et al. (Biochemical and Biophysical Research Communications vol. 376, Issue 1, Nov. 7, 2008, pp. 21-25).*
Hampton et al. (Diabetologia. Apr. 1983;24(4):27881).*
Yamauchi et al. (Nature Medicine 7, 941-946 (2001)).*
Zhou et al. (Biochemical and Biophysical Research Communications vol. 335, Issue 3, Sep. 30, 2005, pp. 937-942).*
Alpha-Linolenic Acid (Omega-3) Walnuts.org Website, accessed Jul. 8, 2017.*
Kalgaonkar et al. European Journal of Clinical Nutrition (2011) 65, 386-393; doi:10.1038/ejcn.2010.266; published online Dec. 15, 2010.*
Pontikis, et al. Journal of Women's Health. Jun. 2011, 20(6): 971-976.*
Sigma Aldrich Fatty Acids Profile Website, Walnuts and Peanuts,www.sigmaaldrich.com/technical-documents/articles/analytical/food-beverage/gc-fattyacids-nuts.html, accessed Jul. 24, 2017.*
Vargas et al. (Metabolism Clinical and Experimental 60 (2011) 1711-1718). (Year: 2011).*
International Search Report (ISR) for PCT/JP2012/073644; I.A. fd: Sep. 14, 2012, dated Dec. 18, 2012 from the Japanese Patent Office, Tokyo, Japan.
International Preliminary Report on Patentability (IPRP), Chapter I of the Patent Cooperation Treaty, including the Written Opinion for PCT/JP2012/073644; I.A. fd: Sep. 14, 2012, dated Mar. 18, 2014, by the International Bureau of WIPO, Geneva, Switzerland.
Brown, JC et al., "Preparation of highly active enterogastrone," Can J Physiol Pharmacol, Jan. 1969; 47(1): 113-114, National Research Council of Canada, Ottawa, Canada.
Falko, JM et al., "Gastric inhibitory polypeptide (GIP) stimulated by fat ingestion in man," J Clin Endocrinol Metab, 1975, 41 (2):260-265, Endocrine Society, Chevy Chase, MD.
Oda, T et al.,eds,. "Alimentary tract," Chapter 3-2 in "An alimentary function and clinical condition," 1981, pp. 201-218, Chugai Medicine Company, Tokyo, Japan.
Gatenby, SJ et al., "Effect of partially depolymerized guar gum on acute metabolic variables in patients with non-insulin-dependent diabetes," Diabet Med, Apr. 1996; 13(4): 358-364, Blackwell Science, Oxford, England.
Ellis, PR et al., "The effect of high-molecular-weight guar gum on net apparent glucose absorption and net apparent insulin and gastric inhibitory polypeptide production in the growing pig: relationship to rheological changes in jejunal digesta," Br J Nutr, Oct. 1995; 74(4): 539-556, CABI Publishing, Wallingford, Oxon, UK.
Nunes CS et al., "Glucose absorption, hormonal release and hepatic metabolism after guar gum ingestion," Reprod Nutr Dev, Jan. 1992; 32(1): 11-20, EDP Sciences, Les Ulis, France.
Morgan, LM et al., "The effect of soluble- and insoluble-fibre supplementation on post-prandial glucose tolerance, insulin and gastric inhibitory polypeptide secretion in healthy subjects," Br J Nutr, Jul. 1990; 64(1): 103-110, CABI Publishing, Wallingford, Oxon, UK.
Requejo, F et al., "Effects of α-glucosidase inhibition and viscous fibre on diabetic control and postprandial gut hormone responses," Diabetic Med, Jul. 1990; 7(6): 515-520, Blackwell Science, Oxford, England.
Morgan, LM et al., "The effect of guar gum on carbohydrate-, fat- and protein-stimulated gut hormone secretion: modification of post-prandial gastric inhibitory polypeptide and gastrin responses," Br J Nutr, May 1985; 53(3): 467-475, CABI Publishing, Wallingford, Oxon, UK.

(Continued)

*Primary Examiner* — Kortney L. Klinkel
*Assistant Examiner* — William Y Lee
(74) *Attorney, Agent, or Firm* — Sterne, Kessler, Goldstein & Fox P.L.L.C.

(57) ABSTRACT

A GIP-increase inhibitor, which may be utilized for producing a medicine, a food, or the like, is provided. The GIP-increase inhibitor contains triacylglycerol in which α-linolenic acid accounts for 10% by mass or more of the constituent fatty acid, as an effective ingredient.

8 Claims, No Drawings

(56) References Cited

OTHER PUBLICATIONS

Kwasowski, P et al., "Effects of fatty acid chain length and saturation on gastric inhibitory polypeptide release in obese hyperglycaemic (ob/ob) mice," Biosci Rep, Aug. 1985; 5(8): 701-705, Plenum Publishing, New York.

Iwasaki, M. et al., Nutritional therapy for improvement of incretin effects on glycemic control in patient with diabetes, ("Incretin o Koryo shita, Shokuji Ryoho") Progress in Medicine, Sep. 10, 2012, 32 (9): 1867-1872, Life Science Co., Ltd., Tokyo, Japan.

Extended European search report, including the supplementary European search report and the European search opinion, for EP Application No. 12831333.5, dated Apr. 1, 2015, European Patent Office, Munich Germany.

Database BIOSIS [Online] Database accession No. PREV200100122615, including abstract for: Kato Moroshi et al, "Effect of alpha-linolenic acid on blood glucose, insulin and GLUT4 protein content of type 2 diabetic mice," J. of Health Science 46(6): 489-492 (Dec. 2000), Biosciences Information Service, Philadelphia, PA.

Yepuri, G et al., "Dietary modulation of body composition and insulin sensitivity during catch-up growth in rats: effects of oils rich in n-6 or n-3 PUFA," Brit J Nutrition, Jan. 2011, 105:1750-1763, CABI Publishing, Wallingford, UK.

Tanaka, T et al, "Cloning and characterization of the rat free fatty acid receptor GPR120: in vivo effect of the natural ligand on GLP-1 secretion and proliferation of pancreatic β cells," Naunyn Schmiedeberg's Arch Pharmacol, Jun. 2008; 377(4-6): 515-522, Springer Verlag, Berlin, Germany.

Adachi, T et al., "Administration of perilla oil coated with Calshell increases glucagon-like peptide secretion," Biol Pharm Bull, May 2008; 31(5): 1021-1023, Pharmaceutical Society of Japan, Tokyo, Japan.

McLeay, LM et al., "Inhibition of ovine gastric acid secretion by intraduodenal long-chain fatty acids," Am J Physiol Gastrointest Liver Physiol, Aug. 1982; 243: G127-G133, American Physiological Society, Bethesda, MD.

Krarup, T et al., "Responses and molecular heterogeneity of IR-GIP after intraduodenal glucose and fat," Am J Physiol Endocrinol Metab, Aug. 1985; 249: E195-E200, American Physiological Society, Bethesda, MD.

Brøns, C. et al., "Impact of short-term high-fat feeding on glucose and insulin metabolism in young healthy men," J Physiol. May 15, 2009;587(Pt 10):2387-97. doi: 10.1113/jphysiol.2009.169078. Epub Mar. 30, 2009.

Ben-Shlomo, S. et al., "Role of glucose-dependent insulinotropic polypeptide in adipose tissue inflammation of dipeptidylpeptidase 4-deficient rats," Obesity (Silver Spring). Nov. 2013;21(11):2331-41. doi: 10.1002/oby.20340. Epub May 29, 2013.

Kirino, Y. et al., "Plasma dipeptidyl peptidase 4 activity correlates with body mass index and the plasma adiponectin concentration in healthy young people,"Endocr J. 2012;59(10):949-53. Epub Jun. 23, 2012.

Ugleholdt, R., "Glucose-dependent Insulinotropic Polypeptide (GIP): From prohormone to actions in endocrine pancreas and adipose tissue," PhD Thesis, Dan Med Bull. Dec. 2011;58(12):B4368 (20 pages).

\* cited by examiner

GIP ELEVATION INHIBITOR

FIELD OF THE INVENTION

The present invention relates to a GIP-increase inhibitor.

BACKGROUND OF THE INVENTION

GIP (Gastric inhibitory polypeptide or glucose-dependent insulinotropic peptide) is one of the gastrointestinal hormones which belong to a glucagon secretin family. GIP is referred to as incretin along with GLP-1 (glucagon-like peptide 1) and has been reported to be secreted from K cells located in the small intestine upon ingestion of lipid and carbohydrate. GIP is also known to possess inhibitory actions against gastric acid secretion and gastric motility (Non Patent Documents 1 to 3). Therefore, it is considered that inhibition of the increase of GIP is effective to promote postprandial digestion and to improve a heavy feeling in the stomach.

According to the previous studies, 3-bromo-5-methyl-2-phenylpyrazolo[1,5-a]pyrimidin-7-ol (BMPP) is known to be a substance inhibiting the functions of GIP, and guar gum or the like is known to be a substance inhibiting the postprandial secretion of GIP (Patent Document 1 and Non Patent Documents 4 to 9). In addition, in recent years, (Pro3) GIP has been known to be a GIP receptor antagonist. However, the safety and effectiveness of these substances have not been sufficiently confirmed.

Meanwhile, perilla and flaxseed are annual plants belonging to Labiatae and Linaceae, respectively. The fat or oil obtained from these plants is characterized in that α-linolenic acid accounts for 50% or more of the constituent fatty acid. Alpha-linolenic acid is one of the ω3-type highly unsaturated fatty acids, which has been reported to possess a function, for example, to enhance secretion of adiponectin (Patent Document 2). Furthermore, it has been reported that the nutrient composition containing protein, lipid such as perilla oil, and carbohydrate possesses an inhibitory effect against the increase of blood glucose level (Patent Document 3) and that perilla oil, linseed oil or the like possesses a tendency to decrease the visceral fat (Patent Document 4).

As for the relationship with GIP, it is known that a long chain fatty acid having 18 or less carbon atoms, such as oleic acid, linoleic acid, linolenic acid, or the like enhances secretion of GIP in blood (Non Patent Document 10).

However, the relationship between fat or oil abundant in α-linolenic acid and secretion of GIP has not been reported at all.

CITATION LIST

Patent Documents

[Patent Document 1] WO-A-01/87341
[Patent Document 2] JP-A-2007-262014
[Patent Document 3] Japanese Patent No. 3545760
[Patent Document 4] JP-A-H10-231495

Non Patent Documents

[Non-Patent Document 1] Brown J C, et al., Canadian J Physiol Pharmacol, 1969, 47:113-114
[Non-Patent Document 2] Falko J M, et al., J Clin Endocrinol Metab, 1975, 41:260-265
[Non-Patent Document 3] Oda T, et al., Chugai-Igakusha, Digestive Tract-Functions and Pathological conditions ("Shoukakan Kinou to Byoutai"), 1981, P205-216
[Non-Patent Document 4] Gatenby S J, et al., Diabet Med, 1996, 13:358-364
[Non-Patent Document 5] Ellis P R, et al., Br J Nutr, 1995, 74:539-556
[Non-Patent Document 6] Simoes Nunes C, et al., Reprod Nutr Dev, 1992, 32:11-20
[Non-Patent Document 7] Morgan L M, et al., Br J Nutr, 1990, 64:103-110
[Non-Patent Document 8] Requejo F, et al., DiabetMed, 1990, 7:515-520
[Non-Patent Document 9] Morgan L M, et al., Br J Nutr, 1985, 53: 467-475
[Non-Patent Document 10] Kwasowski, et al., Bioscience Report 5, 1985:701-705

SUMMARY OF THE INVENTION

The present invention provides the following.

A GIP-increase inhibitor, containing triacylglycerol in which α-linolenic acid accounts for 10% by mass or more of the constituent fatty acid, as an effective ingredient.

An agent for promoting postprandial digestion, containing triacylglycerol in which α-linolenic acid accounts for 10% by mass or more of the constituent fatty acid, as an effective ingredient.

An agent for improving a heavy feeling in the stomach, containing triacylglycerol in which α-linolenic acid accounts for 10% by mass or more of the constituent fatty acid, as an effective ingredient.

A GIP-increase inhibitor, containing a fat and oil composition containing triacylglycerol in which α-linolenic acid accounts for 10% by mass or more of the constituent fatty acid, as an effective ingredient.

An agent for promoting postprandial digestion, containing a fat and oil composition containing triacylglycerol in which α-linolenic acid accounts for 10% by mass or more of the constituent fatty acid, as an effective ingredient.

An agent for improving a heavy feeling in the stomach, containing a fat and oil composition containing triacylglycerol in which α-linolenic acid accounts for 10% by mass or more of the constituent fatty acid, as an effective ingredient.

The present invention also provides the following.

Use of triacylglycerol in which α-linolenic acid accounts for 10% by mass or more of the constituent fatty acid for producing a GIP-increase inhibitor.

Use of triacylglycerol in which α-linolenic acid accounts for 10% by mass or more of the constituent fatty acid for producing an agent for promoting postprandial digestion.

Use of triacylglycerol in which α-linolenic acid accounts for 10% by mass or more of the constituent fatty acid for producing an agent for improving a heavy feeling in the stomach.

The present invention further provides the following.

Triacylglycerol in which α-linolenic acid accounts for 10% by mass or more of the constituent fatty acid to be used for inhibiting GIP-increase.

Triacylglycerol in which α-linolenic acid accounts for 10% by mass or more of the constituent fatty acid to be used for promoting postprandial digestion.

Triacylglycerol in which α-linolenic acid accounts for 10% by mass or more of the constituent fatty acid to be used for improving a heavy feeling in the stomach.

The present invention further provides the following.

Use of triacylglycerol in which α-linolenic acid accounts for 10% by mass or more of the constituent fatty acid for inhibiting GIP-increase.

Use of triacylglycerol in which α-linolenic acid accounts for 10% by mass or more of the constituent fatty acid for promoting postprandial digestion.

Use of triacylglycerol in which α-linolenic acid accounts for 10% by mass or more of the constituent fatty acid for improving a heavy feeling in the stomach.

The present invention further provides the following.

A method for inhibiting GIP-increase comprising administering or having ingest triacylglycerol in which α-linolenic acid accounts for 10% by mass or more of the constituent fatty acid to a subject in need thereof.

A method for promoting postprandial digestion comprising administering or having ingest triacylglycerol in which α-linolenic acid accounts for 10% by mass or more of the constituent fatty acid to a subject in need thereof.

A method for improving a heavy feeling in the stomach comprising administering or having ingest triacylglycerol in which α-linolenic acid accounts for 10% by mass or more of the constituent fatty acid to a subject in need thereof.

The present invention further provides the following.

Non-therapeutic use of triacylglycerol in which α-linolenic acid accounts for 10% by mass or more of the constituent fatty acid for inhibiting GIP-increase.

Non-therapeutic use of triacylglycerol in which α-linolenic acid accounts for 10% by mass or more of the constituent fatty acid for promoting postprandial digestion.

Non-therapeutic use of triacylglycerol in which α-linolenic acid accounts for 10% by mass or more of the constituent fatty acid for improving a heavy feeling in the stomach.

The present invention also provides the following.

Use of triacylglycerol in which α-linolenic acid accounts for 10% by mass or more of the constituent fatty acid for producing a functional food containing a GIP-increase inhibitor.

Use of triacylglycerol in which α-linolenic acid accounts for 10% by mass or more of the constituent fatty acid for producing a functional food containing an agent for promoting postprandial digestion.

Use of triacylglycerol in which α-linolenic acid accounts for 10% by mass or more of the constituent fatty acid for producing a functional food containing an agent for improving a heavy feeling in the stomach.

DETAILED DESCRIPTION OF THE INVENTION

The present invention relates to providing a GIP-increase inhibitor useful for a medicine, a food or the like.

As a result of the investigation for the substances capable of controlling increase of GIP, the present inventors quite unexpectedly have found that triacylglycerol abundant in α-linolenic acid as its constituent fatty acid tends to increase GIP less than other triacylglycerols, while linolenic acid, which is along chain fatty acid, promotes secretion of GIP into blood (Non Patent Document 10).

Since the GIP-increase inhibitor of the present invention possesses the excellent inhibitory effect against the increase of GIP and high safety, it is useful, for example, as a material to promote postprandial digestion and to improve a heavy feeling in the stomach.

The term "inhibition of GIP-increase" in the present invention refers to the inhibition of the increase of GIP secreted from K cells located in the small intestine after ingestion of a meal containing lipids and carbohydrates, especially meals abundant in lipids, meals abundant in triacylglycerols among others. Thus, the term "inhibition of GIP-increase" mainly refers to the inhibition of postprandial GIP-increase.

The term "inhibitory effect against GIP-increase" in the present invention refers to a concept including both of the action to inhibit the secretion of GIP from K cells and the action to decrease the concentration of GIP in blood.

The "inhibitory effect against GIP-increase" in the present invention may be determined using triolein as a standard. For example, the amount of GIP secreted into blood in a test group in which the test substance has been administered to or ingested by the subjects is compared with the amount of GIP in a control group in which triolein has been administered to or ingested by the subjects. If a decrease of the amount of GIP secreted into blood is observed in the test group, the test substance may be considered to possess the inhibitory effect against the increase of GIP. Although statistical technique may not necessarily be used for the evaluation, it is preferable to perform evaluation using a statistical significance test.

The term "non-therapeutic" herein refers to a concept which does not include a therapeutic intervention, i.e., a treatment to a human body by therapy.

The term "improvement" herein refers to amelioration of the disease, symptom or condition, prevention or retardation of deterioration of the disease, symptom or condition, or reversion, prevention or retardation of progression of the disease or symptom.

The content of α-linolenic acid in the total constituent fatty acid in triacylglycerol used in the present invention is 10% by mass (hereinafter simply referred to as "%") or more, preferably 12.5% or more, more preferably 15% or more, even more preferably 20% or more, and preferably 95% or less, more preferably from 12.5 to 95%, more preferably from 15 to 95%, even more preferably from 20 to 95%, from the viewpoint of the inhibitory effect against the increase of GIP.

Although other fatty acid constituting triacylglycerol may be saturated fatty acid or unsaturated fatty acid, it is preferable that the unsaturated fatty acid account for from 70 to 100% of the total constituent fatty acid, from 75 to 100% being more preferable, from 80 to 98% being even more preferable from the viewpoint of the physiological effect. The number of carbon atoms of the unsaturated fatty acid is preferably from 14 to 26, more preferably from 16 to 24, from the viewpoint of the physiological effect.

The content of the saturated fatty acid in the total constituent fatty acid in triacylglycerol is preferably less than 60%, more preferably from 0 to 30%, even more preferably from 0 to 20%, from the standpoint of the appearance and the physiological effect. The number of carbon atoms of the saturated fatty acid is preferably from 14 to 24, more preferably from 16 to 24.

The content of the medium chain fatty acid having 8 to 10 carbon atoms in the total constituent fatty acid in triacylglycerol is preferably less than 5%, more preferably from 0 to 2%, even more preferably from 0 to 1%.

The content of the trans-unsaturated fatty acids in the total constituent fatty acids in triacylglycerol is preferably from 0 to 4%, more preferably from 0.1 to 3.5%, even more preferably from 0.2 to 3%, from the viewpoint of the flavor, physiological effect and appearance.

Triacylglycerol of the present invention may be synthesized according to the conventionally known method by condensation reaction of glycerol and fatty acid. It may also be obtained by the ester exchange reaction or the like of the edible fat or oil mentioned below so as to make the desirable fatty acid composition according to the conventional method, followed by purification if needed.

Triacylglycerol in the present invention may be used as a fat or oil composition containing triacylglycerol. The fat or oil in the composition may contain one or more of diacylglycerol and monoacylglycerol, besides triacylglycerol.

The content of triacylglycerol in the fat or oil composition is preferably 85% or more, more preferably 88% or more, more preferably 90% or more, even more preferably 92% or more, and preferably 99.8% or less, more preferably 99.5% or less, even more preferably 99% or less, and preferably from 88 to 99.8%, more preferably from 90 to 99.5%, even more preferably from 92 to 99%, from the viewpoint of the inhibitory effect against the increase of GIP.

The content of diacylglycerol in the fat and oil composition is preferably from 0 to 5%, more preferably from 0 to 4%, even more preferably from 0.1 to 3%, from the viewpoint of the industrial productivity and stability. The content of monoacylglycerol is preferably from 0 to 5%, more preferably from 0 to 2%, even more preferably from 0.1 to 2%, from the viewpoint of the flavor and industrial productivity.

It is preferable that the constituent fatty acid of diacylglycerol and monoacylglycerol be the same as triacylglycerol from a viewpoint of the physiological effect and production.

The content of the free fatty acid (salt) contained in the fat or oil composition of the present invention is preferably 5% or less, more preferably from 0 to 2%, even more preferably from 0 to 1%, from the viewpoint of the flavor and industrial productivity of the fat or oil.

The edible fat or oil usable for the fat and oil composition of the present invention is not particularly limited and any of vegetable fat or oil and animal fat or oil may be used. Specific materials include rapeseed oil (canola oil), sunflower oil, corn oil, soybean oil, linseed oil, perilla oil, rice oil, safflower oil, cottonseed oil, palm oil, copra oil, olive oil, grape oil, avocado oil, sesame oil, peanut oil, macadamia nut oil, hazelnut oil, walnut oil, lard, beef fat, chicken fat, butterfat, fish oil, or the like. Among these, it is preferable that linseed oil, perilla oil, or the like be used since they are abundant in $\alpha$-linolenic acid.

Although the products obtained by fractionation and mixing of these fats or oils or those obtained by adjusting the fatty acid composition via hydrogenation, ester exchange reaction or the like may be utilized, the products which have not been hydrogenated are preferable, since the content of trans unsaturated fatty acid in the total fatty acid constituting the fat or oil may be reduced. Commercially available products may also be used.

In addition, it is preferable that the fat or oil composition of the present invention contain from 0.01 to 2%, more preferably from 0.01 to 1%, even more preferably from 0.01 to 0.5%, of the antioxidant in the composition, from the viewpoint of the oxidative stability upon storage and cooking. The antioxidant includes one or more selected from a natural antioxidant, tocopherol, ascorbyl palmitate, ascorbyl stearate, butylated hydroxytoluene (BHT), butylated hydroxyanisole (BHA), or the like.

As will be shown later in Example, triacylglycerol abundant in $\alpha$-linolenic acid in its constituent fatty acid exhibited a significant inhibitory effect against the increase of GIP compared with triolein. Therefore, such triacylglycerol and the fat or oil composition containing the triacylglycerol may be used to inhibit increase of GIP. In addition, since inhibition of the increase of GIP results in preventing the inhibition of gastric acid secretion and the inhibition of gastric motility, the triacylglycerol and the fat or oil composition of the present invention may be used to promote postprandial digestion and to improve a heavy feeling in the stomach and gastric acid secretion ability. Such usage may be a use for human beings, non-human animals or samples derived therefrom, and may be a use for therapeutic or non-therapeutic purposes.

Furthermore, the triacylglycerol and the fat or oil composition of the present invention may be used as a GIP-increase inhibitor, an agent for promoting postprandial digestion based on the preventing effect against the increase of GIP, an agent for improving a heavy feeling in the stomach, an agent for improving the gastric acid secretion ability, or the like (hereinafter referred to as "GIP-increase inhibitor or the like"), and as a raw material to produce these agents. In this case, the triacylglycerol and the fat or oil composition may be used alone or in combination with any of the below-mentioned substances acceptable to be blended, such as a carrier or the like optionally selected as needed, in producing the GIP-increase inhibitor or the like. Note that these preparations may be produced according to ordinary methods depending on the substances to be blended.

The GIP-increase inhibitor or the like may be used as an effective ingredient to be blended for pharmaceutical products for human beings or animals, quasi-drugs, food or animal food which exert effects for inhibiting the increase of GIP, promoting the postprandial digestion, improving a heavy feeling in the stomach, or the like. The GIP-increase inhibitor or the like may also be applied to a food, a functional food, a patient food and a specified health food having a concept for inhibiting the increase of GIP, promoting the postprandial digestion and improving a heavy feeling in the stomach, with an indication of such concept as needed.

When the GIP-increase inhibitor or the like of the present invention is used as an effective ingredient of the pharmaceutical products, such pharmaceutical products may be administered in any administration form. Examples of the administration form include oral administration, enteral administration, transmucosal administration, and injection. Examples of the dosage form for oral administration include a tablet, a coated tablet, a capsule, a granule, a powder medicine, a powder, a sustained-release preparation, a suspension, an emulsion, an internal use liquid, a sugar coated tablet, a pill, a fine granule, a syrup and an elixir. Examples of the dosage form for parenteral administration include an intravenous injection, an intramuscular injection, an inhalation, an infusion, a suppository, an inhalant, an epicutaneous drug, an eye drop, and a nasal drop.

In such preparations, the GIP-increase inhibitor or the like of the present invention may be used alone or in combination with other pharmaceutically acceptable carriers. Examples of such carriers include an excipient, a binder, a disintegrant, a lubricant, a diluent, an osmotic pressure adjuster, a fluidity promoter, an absorption aid, a pH adjuster, an emulsifier, an antiseptic, a stabilizer, an antioxidant, a colorant, a UV absorber, a moisturizer, a thickener, a brightening agent, an activity enhancer, an anti-inflammatory agent, a germicide, a taste masking agent, an odor masking agent, a filler, a surfactant, a dispersant, a buffer, a preservative, a flavoring agent and a coating agent.

Oral administration is preferable among these administration forms. The content of triacylglycerol and the fat or oil composition in the preparation for the oral administration containing the GIP-increase inhibitor or the like is usually from 0.01 to 100%, preferably from 0.1 to 100%, more preferably from 1 to 100%, even more preferably from 5 to 100% of the total mass of the preparation.

Furthermore, when the GIP-increase inhibitor or the like of the present invention is blended and used as an effective ingredient of the foods, the GIP-increase inhibitor or the like may be applied to the functional foods such as a cosmetic food, a patient food, a nutrient function food, a health claim food, a functional claim food, a supplement food, a health functional food, a specified health food or the like, having a concept for inhibiting the increase of GIP, promoting the postprandial digestion and improving a heavy feeling in the stomach, with an indication of such concept as needed, as well as common food. Note that the functional food is the food having a license to indicate the function and is distinguished from common food.

When the GIP-increase inhibitor or the like of the present invention is used as an effective ingredient of the food, the form of the food may be a solid, a semi-solid, or a liquid. Examples of the food include bread, noodles, confectionery such as a cookie, jellies, a dairy product, a frozen food, a convenience food, a processed starch product, a processed meat product, other processed foods, beverages such as a coffee beverage, soups, seasonings, and a dietary supplement, and raw materials thereof. Further, the form may be, as is the case of the above-mentioned oral preparation, a tablet form, a pill form, a capsule form, a liquid form, a syrup form, a powder form, a granule form, or the like.

In order to prepare the foods in various forms, the GIP-increase inhibitor or the like may be used alone, or in combination with other food materials, as well as a solvent, a softener, oil, an emulsifier, an antiseptic, a fragrance, a stabilizer, a colorant, a UV absorber, an antioxidant, a humectant, a thickener, or the like, as needed.

The content of triacylglycerol and the fat or oil composition in the food containing the GIP-increase inhibitor or the like varies depending on their type of usage and is usually from 0.01 to 50% in the form of beverage, preferably from 0.01 to 20%, more preferably from 0.01 to 10%, more preferably from 1 to 50%, even more preferably from 5 to 50%. The content in the form of a solid food such as a tablet, a processed food or the like is usually from 0.001 to 100%, preferably from 0.01 to 80%, more preferably from 0.01 to 50%, more preferably from 1 to 80%, even more preferably from 5 to 50%.

When the GIP-increase inhibitor or the like of the present invention is used as an effective ingredient of the animal food, examples of the food include the food for livestock such as a cow, a pig, a chicken, a sheep, a horse or the like, the food for small animals such as a rabbit, a rat, a mouse or the like, the food for fish and shellfish such as a tuna, an eel, a sea bream, an yellowtail, a prawn or the like, the food for pets such as a dog, a cat, a small bird, a squirrel or the like.

In addition, when producing the animal food, the GIP-increase inhibitor or the like may be blended alone or in combination with the commonly used raw materials for animal food such as a meat of a cow, a pig, a sheep or the like, protein, cereals, bran, lees, sugars (carbohydrates), vegetables, vitamins, minerals, as well as commonly used agents for animal food such as a gelation agent, an excipient, a pH adjuster, a seasoning, an antiseptic, a nutritional supplement or the like as needed to produce the animal food according to a conventional method.

The content of triacylglycerol and the fat or oil composition in the animal food containing the GIP-increase inhibitor or the like varies depending on their type of usage and is usually from 0.01 to 50% in the form of liquid, preferably from 0.01 to 20%, more preferably from 0.01 to 10%, more preferably from 1 to 50%, even more preferably from 5 to 50%. The content in the form of a solid such as a tablet, a processed product or the like is usually from 0.01 to 100%, preferably from 0.01 to 80%, more preferably from 0.01 to 50%, more preferably from 1 to 80%, even more preferably from 5 to 50%.

The amount to administer or ingest of the above-mentioned preparation or the like may vary depending on the condition, body weight, sex and age of the patient or other factors and is preferably from 0.1 to 20 g as triacylglycerol abundant in α-linolenic acid per one adult per day usually in the case of oral administration or oral ingestion. The above-mentioned preparations may be administered or ingested in accordance with any administration regimen and is preferably administered or ingested in one to several divided doses per day.

The subject of administration or ingestion may be a tissue, an organ, a cell or the fractions thereof derived from animals. The tissue, organ, cell or the fractions thereof is preferably those of the natural origin or biologically modified or bioengineered, which possess the ability to secret GIP.

The GIP-increase inhibitor or the like of the present invention is administered or ingested preferably during or before meal, especially preferably during meal or within 5 min to 30 min prior to meal. The nutrition composition of the meal is not particularly limited and is a usual meal containing carbohydrate, lipid, protein, vitamin and mineral. As for its energy composition, the ratio of carbohydrate and lipid is preferably from 100:0 to 10:90. The preferred subject of the administration or ingestion is a human who needs the inhibition of GIP-increase, a human who needs the promotion of postprandial digestion, a human who needs the improvement of a heavy feeling in the stomach, a human who needs the prevention of the inhibition of gastric acid secretion, or a human who needs the prevention of the inhibition of gastric motility. Healthy humans including a human who desires the inhibition of GIP-increase, a human who desires the promotion of postprandial digestion, a human who desires the improvement of a heavy feeling in the stomach, a human who desires the prevention of the inhibition of gastric acid secretion, or a human who desires the prevention of the inhibition of gastric motility are also preferred. Furthermore, a human whose fasting blood GIP level is 30 pg/mL or more, or a human whose basal gastric secretion is 30 mL/hour or less in the gastric secretion function test is preferred.

The present invention also provides the following.
(1) Use of triacylglycerol in which α-linolenic acid accounts for 10% by mass or more of the constituent fatty acid in a functional food for inhibiting GIP-increase.
(2) Use of triacylglycerol in which α-linolenic acid accounts for 10% by mass or more of the constituent fatty acid in a functional food for promoting postprandial digestion.
(3) Use of triacylglycerol in which α-linolenic acid accounts for 10% by mass or more of the constituent fatty acid in a functional food for improving a heavy feeling in the stomach.
(4) Use according to any one of the items (1) through (3), wherein the fat or oil composition containing triacylglycerol in which α-linolenic acid accounts for 10% by mass or more of the constituent fatty acid is used.
(5) Use according to item (4), wherein the fat or oil composition contains 85% by mass or more of the triacylglycerol.

(6) Use according to any one of the items (1) through (5), wherein the functional food for inhibiting GIP-increase, the functional food for promoting postprandial digestion, or the functional food for improving a heavy feeling in the stomach is administered or ingested during meal or within 5 min to 30 min prior to meal.

(7) Use according to any one of the items (1) through (6), wherein the functional food for inhibiting GIP-increase, the functional food for promoting postprandial digestion, or the functional food for improving a heavy feeling in the stomach is administered to or ingested by a human whose fasting blood GIP level is 30 pg/mL or more, or a human whose basal gastric secretion is 30 mL/hour or less.

EXAMPLES

Composition of the Constituent Fatty Acid of the Oil

Derivatization to Fatty Acid

To 25 mg of the fat or oil weighed was added 2.0 mL of 0.5 mol/L sodium hydroxide/methanol solution and heated for 7 min at 100° C. To the mixture was then added 2 mL of boron trifluoride/methanol reagent and heated for 5 min at 100° C. After cooling, to the mixture were added 1 mL of 2,2,4-trimethylpentane and 4 mL of saturated sodium chloride aqueous solution. After shaking, the layer of 2,2,4-trimethylpentane was recovered and subjected to gas chromatographic analysis.

Summary of Gas Chromatography System

Gas chromatography: 6890N Network GC System (trade name, manufactured by Agilent Technologies Ltd.)
Autosampler: 7683 Series Injector (trade name, manufactured by Agilent Technologies Ltd.)
Conditions for Gas Chromatography
Temperature: Injection port: 250° C., FID detector: 250° C.
Oven: Initial temperature: 50° C., Initial temperature retention time: 1 min, Temperature increasing rate: 25° C./min (Final temperature: 120° C.), 2° C./min (Final temperature: 250° C.)
Flow rate: 1.49 mL/min
Injection mode: Split (Split ratio: 1/100)
Column: DB-23 (trade name, 0.25 μm×250 μm×30 m, manufactured by Agilent Technologies Ltd.)

The fatty acid composition of the oil was calculated according to the following equation.

Fatty acid composition(%)=$A/B$×100

(wherein A indicates the peak area of each fatty acid and B indicates the total peak area.)

Glyceride Composition of the Oil

A glass sample vial was charged with about 10 mg of the oil sample and 0.5 mL of a trimethylsilylation agent ("Silylation Agent TH" manufactured by Kanto Kagaku), tightly plugged, and heated for 15 min at 70° C. After adding 1.0 mL of water and 1.5 mL of hexane, the vial was shaken. After still standing, the upper layer was subjected to gas chromatography (GLC) analysis.

GLC Conditions

Gas chromatography: 6890N Network GC System (trade name, manufactured by Agilent Technologies Ltd.)
Integrator: Chemistation B 02.01 SR2 (manufactured by Agilent Technologies Ltd.)
Detector: FID, T=350° C.
Oven temperature: Temperature increased from 80° C. to 340° C. at 10° C./min, retention time 15 min
Carrier gas: 1.0 mL He/min
Injection mode: Split (1:50), T=320° C.
Column: DB-1ht (manufactured by Agilent J&W Ltd.)

Example 1

Study of Inhibitory Effect Against the Increase of GIP

For evaluation, perilla oil (Summit Oil Mill Co., Ltd.), linseed oil (Summit Oil Mill Co., Ltd.), soybean oil (Summit Oil Mill Co., Ltd.), and canola oil (Summit Oil Mill Co., Ltd.) were used as the test group. Triolein (Sigma) was used as the control group. The fatty acid composition and the glyceride composition of each oil composition are shown in Table 1 and Table 2, respectively.

TABLE 1

| | | Fatty acid composition (%) | | | | |
|---|---|---|---|---|---|---|
| | | Triolein | Perilla oil | Linseed oil | Soybean oil | Canola oil |
| C14:0 | Myristic acid | 0.0 | 0.0 | 0.0 | 0.1 | 0.1 |
| C16:0 | Palmitic acid | 0.0 | 6.0 | 5.2 | 10.2 | 4.2 |
| C16:1 | Palmitoleic acid | 0.0 | 0.0 | 0.0 | 0.0 | 0.0 |
| C18:0 | Stearic acid | 0.0 | 2.0 | 3.7 | 3.9 | 1.9 |
| C18:1 | Oleic acid | 100.0 | 14.8 | 20.3 | 21.7 | 62.0 |
| C18:2 | Linoleic acid | 0.0 | 15.4 | 15.6 | 53.7 | 19.4 |
| C18:3 | γ-Linolenic acid | 0.0 | 0.0 | 0.0 | 0.0 | 0.0 |
| C18:3 | α-Linolenic acid | 0.0 | 58.1 | 51.3 | 7.3 | 8.2 |
| C20:0 | Arachidic acid | 0.0 | 0.2 | 0.2 | 0.4 | 0.6 |
| C20:4 | Arachidonic acid | 0.0 | 0.0 | 0.0 | 0.0 | 0.0 |
| C20:5 | Icosapentaenoic acid | 0.0 | 0.0 | 0.0 | 0.0 | 0.0 |
| C22:0 | Behenic acid | 0.0 | 0.0 | 0.0 | 0.3 | 0.0 |
| C22:5 | Docosapentaenoic acid | 0.0 | 0.0 | 0.0 | 0.0 | 0.0 |
| C22:6 | Docosahexaenoic acid | 0.0 | 0.0 | 0.0 | 0.0 | 0.0 |
| Others | | | 3.5 | 3.7 | 2.4 | 3.6 |

TABLE 2

| | Triolein | Perilla oil | Linseed oil | Soybean oil | Canola oil |
|---|---|---|---|---|---|
| MAG | 0.0 | 0.0 | 0.0 | 0.1 | 0.0 |
| DAG | 0.0 | 2.8 | 3.3 | 2.0 | 2.1 |
| TAG | 100.0 | 96.5 | 95.7 | 97.4 | 96.6 |

MAG: monoacylglycerol
DAG: diacylglycerol
TAG: triacylglycerol

The emulsion used was prepared by mixing each oil composition as a lipid, glucose (Wako Purechemical Industries, Ltd.) as a carbohydrate, 0.2% egg-yolk lecithin (Wako Purechemical Industries, Ltd.), and distilled water in the composition shown in Table 3, followed by ultrasound treatment, so that the load of the lipid and carbohydrate was 2 mg/g body weight, respectively.

Seven-week-old male mice (C57BL/6J, CLEA Japan, Inc.) were preliminary raised by feeding with the standard powder feed CE-2 (CLEA Japan, Inc.) for one week. The room temperature was 22+/−2° C. and the humidity was 55+/−10% in the raising environment. The lighting time was from 7 to 19 o'clock. After that, the mice were fasted for 17 hours. The initial blood samples were taken from the orbital vein plexus (heparinized micro-hematocrit tubes, manufactured by VITREX) under anesthesia with diethylether. Ten, 30 and 60 min after administrating each emulsion (n=10) into the stomach, the blood samples were taken from the orbital vein plexus under anesthesia with diethylether. The blood collected was stored in ice and centrifuged at 11000 rpm for 6 min to obtain the plasma. The plasma obtained was stored at −80° C. until measurement. The concentration of GIP in the plasma was determined by ELISA method (Rat/Mouse GIP (Total) ELISA Kit, Linco Research/Millipore Co.) and the area under curve (AUC) of the graph was calculated.

The relative values of GIP AUC until 60 min after administration of each oil composition, when the AUC (increase against the initial value) of the concentration of GIP in the plasma until 60 min after administration of the emulsion for triolein administration group (control group) is taken as 100, are shown in Table 4.

The values are shown in mean+/−standard deviation. The t-test for the control group was performed for the statistical significance test between the groups. The p value of 0.05 or less in the two-tail test was judged to be significant difference and shown as * (vs. triolein) in the table.

TABLE 3

| Emulsion composition | |
|---|---|
| | Composition (%) |
| Fat or oil composition | 5.0 |
| Glucose | 5.0 |
| Egg-yolk lecithin | 0.2 |
| Distilled water | 89.8 |
| Total | 100.0 |

TABLE 4

| GIP AUC 60 min after administration of emulsion (Relative value vs. triolein) | |
|---|---|
| Triolein | 100.0 ± 3.5 |
| *Perilla* oil | 77.0 ± 3.8* |
| Linseed oil | 75.0 ± 5.9* |
| Soybean oil | 111.2 ± 12.7 |
| Canola oil | 80.4 ± 4.2 |

Mean ± SE.
*P < 0.05 vs. triolein

The AUC of the concentration of GIP in plasma until 60 min after the administration of perilla oil and linseed oil, which are abundant in α-linolenic acid, was significantly lower than that of triolein. The AUC for the increase of GIP in soybean oil and canola oil groups, which are used as the common edible oil, is not significantly different from triolein.

Example 2

Study of Inhibitory Effect Against the Increase of GIP at Low Dosage

For evaluation, canola oil, 30% of the total amount of which is replaced with perilla oil, and 100% canola oil were used as the test group and the control group, respectively. The fatty acid composition and glyceride composition of each oil composition are shown in Table 5 and Table 6, respectively. Perilla oil (Summit Oil Mill Co., Ltd.) and canola oil (Summit Oil Mill Co., Ltd.) were used to prepare the test oil similarly to Example 1.

TABLE 5

| Fatty acid composition (%) | | | |
|---|---|---|---|
| | | Canola oil | Canola oil 30% replaced with *perilla* oil |
| C14:0 | Myristic acid | 0.1 | 0.1 |
| C16:0 | Palmitic acid | 4.2 | 4.2 |
| C16:1 | Palmitoleic acid | 0.0 | 0.2 |
| C18:0 | Stearic acid | 1.9 | 1.5 |
| C18:1 | Oleic acid | 62.0 | 50.5 |
| C18:2 | Linoleic acid | 19.4 | 18.1 |
| C18:3 | γ-Linolenic acid | 0.0 | 0.0 |
| C18:3 | α-Linolenic acid | 8.2 | 25.1 |
| C20:0 | Arachidic acid | 0.6 | 0.4 |
| C20:4 | Arachidonic acid | 0.0 | 0.0 |
| C20:5 | Icosapentaenoic acid | 0.0 | 0.0 |
| C22:0 | Behenic acid | 0.0 | 0.0 |
| C22:5 | Docosapentaenoic acid | 0.0 | 0.0 |
| C22:6 | Docosahexaenoic acid | 0.0 | 0.0 |
| Others | | 3.6 | 0.0 |

TABLE 6

| Glyceride composition (%) | | |
|---|---|---|
| | Canola oil | Canola oil 30% replaced with *perilla* oil |
| MAG | 0.0 | 0.1 |
| DAG | 2.1 | 1.8 |
| TAG | 96.6 | 98.0 |

The emulsion used was prepared by mixing each oil composition as a lipid, amioca starch (National Starch) obtained by gelatinization for 15 min at 120° C. as a carbohydrate, 0.2% egg-yolk lecithin (Wako Purechemical Industries, Ltd.), 1% bovine serum albumin (Sigma) and distilled water in the composition shown in Table 7, followed by ultrasound treatment, so that the load of the lipid and carbohydrate was 2 mg/g body weight, respectively.

Seven-week-old male mice (C57BL/6J, CLEA Japan, Inc.) were preliminary raised by feeding with the standard powder feed CE-2 (CLEA Japan, Inc.) for one week. The room temperature was 22+/−2° C. and the humidity was 55+/−10% in the raising environment. The lighting time was from 7 to 19 o'clock. After that, the mice were fasted for 17 hours. The initial blood samples were taken from the orbital vein plexus (heparinized micro-hematocrit tubes, manufactured by VITREX) under anesthesia with diethylether. Ten, 30 and 60 min after administrating each emulsion (n=16) into the stomach, the blood samples were taken from the orbital vein plexus under anesthesia with diethylether. The blood collected was stored in ice and centrifuged at 11000 rpm for 6 min to obtain the plasma. The plasma obtained was stored at −80° C. until measurement. The concentration of GIP in the plasma was determined by ELISA method (Rat/Mouse GIP (Total) ELISA Kit, Linco Research/Millipore Co.) and the area under curve (AUC) of the graph was calculated.

The relative values of GIP AUC until 60 min after administration of each oil composition, when the AUC of the concentration of GIP in the plasma until 60 min after administration of the emulsion for canola oil administration group (control group) is taken as 100, are shown in Table 8.

The values are shown in mean+/−standard deviation. The t-test for the control group was performed as the statistical significance test between the groups. The p value of 0.05 or less in the two-tail test was judged to be significant difference and shown as * (vs. canola oil) in the table.

TABLE 7

Emulsion composition

| | Composition (%) |
|---|---|
| Fat or oil composition | 5.0 |
| Starch | 5.0 |
| BSA | 1.0 |
| Egg-yolk lecithin | 0.2 |
| Distilled water | 88.8 |
| Total | 100.0 |

TABLE 8

GIP AUC 60 min after administration of emulsion (Relative value vs. canola oil)

| Canola oil | 100.0 ± 4.3 |
|---|---|
| Canola oil 30% replaced with *perilla* oil | 84.4 ± 4.5* |

Mean ± SE.
*P < 0.05 vs. canola oil

The AUC of the concentration of GIP in plasma until 60 min after the administration of canola oil 30% replaced with perilla oil, which is more abundant in α-linolenic acid, was significantly lower than that of 100% canola oil. It was suggested that α-linolenic acid may exhibit the decreasing effect of GIP even at a low dosage.

Example 3

Study of Inhibitory Effect Against the Increase of GIP at Low Dosage

For evaluation, canola oil 20% of the total amount replaced with linseed oil so that the content of α-linolenic acid was about 20% and 100% corn oil were used as the test group and the control group, respectively. The fatty acid composition of each oil composition is shown in Table 9.

TABLE 9

| | | Fatty acid composition (%) | |
|---|---|---|---|
| | | Corn oil | Canola oil 20% replaced with linseed oil |
| C14:0 | Myristic acid | 0.1 | — |
| C16:0 | Palmitic acid | 10.7 | 4.3 |
| C16:1 | Palmitoleic acid | — | 0.2 |
| C18:0 | Stearic acid | 1.9 | 2.2 |
| C18:1 | Oleic acid | 30.4 | 51.7 |
| C18:2 | Linoleic acid | 53.0 | 18.7 |
| C18:3 | γ-Linolenic acid | — | 0.0 |
| C18:3 | α-Linolenic acid | 1.5 | 20.6 |
| C20:0 | Arachidic acid | 0.5 | 0.5 |
| C20:4 | Arachidonic acid | 0.0 | — |
| C20:5 | Icosapentaenoic acid | 0.0 | — |
| C22:0 | Behenic acid | 0.0 | — |
| C22:5 | Docosapentaenoic acid | 0.0 | — |
| C22:6 | Docosahexaenoic acid | 0.0 | — |
| Others | | 1.9 | 1.8 |

The emulsion used was prepared by mixing each oil composition as a lipid, amioca starch (National Starch) obtained by gelatinization for 15 min at 120° C. as a carbohydrate, 0.2% egg-yolk lecithin (Wako Purechemical Industries, Ltd.), 1% bovine serum albumin (Sigma) and distilled water in the composition shown in Table 10, followed by ultrasound treatment, so that the load of the lipid and carbohydrate was 2 mg/g body weight, respectively.

Seven-week-old male mice (C57BL/6J, CLEA Japan, Inc.) were preliminary raised by feeding with the standard powder feed CE-2 (CLEA Japan, Inc.) for one week. The room temperature was 22+/−2° C. and the humidity was 55+/−10% in the raising environment. The lighting time was from 7 to 19 o'clock. After that, the mice were fasted for 17 hours. The initial blood samples were taken from the orbital vein plexus (heparinized micro-hematocrit tubes, manufactured by VITREX) under anesthesia with diethylether. Ten, 30 and 60 min after administrating each emulsion (n=16) into the stomach, the blood samples were taken from the orbital vein plexus under anesthesia with diethylether. The blood collected was stored in ice and centrifuged at 11000 rpm for 6 min to obtain the plasma. The plasma obtained was stored at −80° C. until measurement. The concentration of GIP in the plasma was determined by ELISA method (Rat/Mouse GIP (Total) ELISA Kit, Linco Research/Millipore Co.).

The maximum increase value of GIP after administration of canola oil replaced with linseed oil, when the maximum increase value of GIP after administration of the emulsion in the corn oil administration group (control group) is taken as 100, is shown in Table 11. Note that the maximum increase value of GIP is the maximum value at a time point when the average value of the concentration of GIP was the highest, which was 10 min after the administration of the emulsion for each group.

The values are shown in mean+/−standard deviation. The t-test for the control group was performed as the statistical significance test between the groups. The p value of 0.05 or less in the two-tail test was judged to be significant difference and shown as * (vs. corn oil) in the table.

TABLE 10

Emulsion composition

| | Composition (%) |
|---|---|
| Fat and oil composition | 5.0 |
| Starch | 10.0 |
| BSA | 0.2 |
| Egg-yolk lecithin | 1.0 |
| Distilled water | 83.8 |
| Total | 100.0 |

TABLE 11

Maximum GIP increase after administration
of emulsion (Relative value vs. corn oil)

| | |
|---|---|
| Corn oil | 100.0 ± 6.6 |
| Canola oil 20% replaced with linseed oil | 81.7 ± 4.3* |

Mean ± SE.
*$P < 0.05$ vs. corn oil

The maximum increase of GIP after the administration of canola oil 20% replaced with linseed oil, which is more abundant in α-linolenic acid, was significantly lower than that of 100% corn oil. It was suggested that α-linolenic acid may exhibit the inhibitory effect against the increase of GIP even at a low dosage.

What is claimed is:

1. A method for inhibiting a postprandial increase in secretion of gastric inhibitory polypeptide (GIP) from the small intestine, the method comprising orally administering to a subject in need thereof, or ingestion by the subject of, triacylglycerol in which α-linolenic acid accounts for 20% by mass or more of the constituent fatty acid, the administering or ingestion occurring during, or within 30 min prior to, a meal comprising lipid and carbohydrate, and wherein the subject is a human whose fasting blood GIP level is 30 pg/mL or more, or a human whose basal gastric secretion is 30 mL/hour or less, wherein the ingestion or administering of the triacylglycerol inhibits the postprandial increase in secretion of gastric inhibitory polypeptide (GIP).

2. The method according to claim 1, wherein a fat and oil composition containing triacylglycerol in which α-linolenic acid accounts for 20% by mass or more of the constituent fatty acid is administered to or ingested by the subject.

3. The method according to claim 2, wherein the fat and oil composition contains 85% by mass or more of the triacylglycerol.

4. The method according to claim 1, wherein the triacylglycerol is administered to or ingested by the subject during a meal or within 5 min prior to a meal.

5. The method according to claim 1, wherein the subject is also in need of preventing an inhibition of gastric acid secretion, or preventing an inhibition of gastric motility.

6. The method according to claim 1, wherein α-linolenic acid accounts for 20 to 95% by mass of the constituent fatty acid of the triacylglycerol.

7. The method according to claim 6, wherein the triacylglycerol is administered to or ingested by the subject during a meal or within 5 min prior to a meal.

8. The method according to claim 6, wherein the subject is also in need of preventing an inhibition of gastric acid secretion, or preventing an inhibition of gastric motility.

\* \* \* \* \*